United States Patent
Zhang et al.

(10) Patent No.: US 11,878,294 B2
(45) Date of Patent: Jan. 23, 2024

(54) PROCESS FOR THE HYDROFORMYLATION OF OLEFINS USING A COBALT PRECATALYST AND A DIPHOSPHINE LIGAND

(71) Applicant: EVONIK OPERATIONS GMBH, Essen (DE)

(72) Inventors: Baoxin Zhang, Rostock (DE); Armin Börner, Rostock (DE); Robert Franke, Marl (DE)

(73) Assignee: EVONIK OPERATIONS GMBH, Essen (DE)

( * ) Notice: Subject to any disclaimer, the term of this patent is extended or adjusted under 35 U.S.C. 154(b) by 0 days.

(21) Appl. No.: 18/182,063

(22) Filed: Mar. 10, 2023

(65) Prior Publication Data

US 2023/0321642 A1    Oct. 12, 2023

(30) Foreign Application Priority Data

Mar. 18, 2022 (EP) .................................... 22163016

(51) Int. Cl.
*C07C 45/50* (2006.01)
*B01J 31/24* (2006.01)
*B01J 27/12* (2006.01)
*C07C 45/28* (2006.01)

(52) U.S. Cl.
CPC .............. *B01J 31/24* (2013.01); *B01J 27/12* (2013.01); *C07C 45/28* (2013.01); *B01J 2231/321* (2013.01)

(58) Field of Classification Search
CPC .............................. C07C 45/505; B01J 31/24
See application file for complete search history.

(56) References Cited

U.S. PATENT DOCUMENTS 11,560,348 B2    1/2023    Zhang et al.

FOREIGN PATENT DOCUMENTS

| EP | 3 888 790 A1 | 10/2021 |
| EP | 4 098 646 A1 | 12/2022 |
| WO | 2019/237090 A1 | 12/2019 |

OTHER PUBLICATIONS

Extended European Search Report dated Nov. 29, 2022 for European Patent Application No. 22163016.3 (12 pages in German with English Translation).
Hood, Drew M., et al. Highly active cationic cobalt (II) hydroformylation catalysts. Science. Jan. 31, 2020. vol. 367, pp. 542-548.
Zhang, Baoxin, et al. Hydroformylation. ChemTexts. Dec. 2, 2021. vol. 8:2, pp. 1-26.
Franke, Robert, et al. Applied Hydroformylation. Chem Rev. Nov. 14, 2012. vol. 112, pp. 5675-5732.
Delolo, Fabio et al. Cobalt-Catalyzed Hydroformylation under Mild Conditions in the Presence of Phosphine Oxides. ACS Sustainable Chem. Eng. Mar. 31, 2021. vol. 9, pp. 5148-5154.

*Primary Examiner* — Sikarl A Witherspoon
(74) *Attorney, Agent, or Firm* — Smith, Gambrell & Russell, LLP

(57) ABSTRACT

Process for the hydroformylation of olefins using a cobalt precatalyst and a diphosphine ligand.

13 Claims, No Drawings

PROCESS FOR THE HYDROFORMYLATION OF OLEFINS USING A COBALT PRECATALYST AND A DIPHOSPHINE LIGAND

The invention relates to a process for the hydroformylation of olefins using a cobalt precatalyst and a diphosphine ligand.

The use of cobalt catalysts in hydroformylation is described in Hood et al. "Highly active cationic cobalt (II) hydroformylation catalysts", Science, volume 367, number 6477, pages 542-548 (2020). In this process, the diphosphine ligands used are always employed in a ratio of 1:1 to cobalt. In the case of Rh, the ligand was employed in a significant excess (L/Rh=400-1600:1).

The technical object underlying the present invention is that of providing a process with which olefins can be hydroformylated. In the process, an increased yield should be achieved.

This object is achieved by a process according to claim 1.
Process comprising the process steps of:
a) adding an olefin;
b) adding a cobalt precatalyst;
c) adding a ligand (L) having the structure (I):

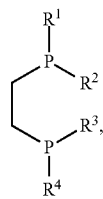

(I)

where $R^1$, $R^2$, $R^3$, $R^4$ are selected from:
—H, —($C_1$-$C_{12}$)-alkyl, —($C_6$-$C_{20}$)-aryl;
wherein the ligand is added in a molar ratio to cobalt of L/Co=<0.95/1;
d) supplying of syngas;
e) heating the reaction mixture from a) to d), to convert the olefin into an aldehyde.

Process steps a) to d) can take place here in any desired order.

Addition of the ligand in a molar ratio to cobalt of L/Co=less than 0.95 to 1 means that the ligand (L) is being added substoichiometrically in respect of the metal (Co).

In one variant of the process, $R^1$, $R^2$, $R^3$, $R^4$ are selected from: —($C_1$-$C_{10}$)-alkyl, —($C_6$-$C_{20}$)-aryl.
In one variant of the process, $R^1$, $R^2$ are —($C_6$-$C_{20}$)-aryl.
In one variant of the process, $R^1$, $R^2$ are -Ph.
In one variant of the process, $R^1$, $R^3$ are —($C_6$-$C_{20}$)-aryl.
In one variant of the process, $R^1$, $R^3$ are -Ph.
In one variant of the process the ligand has the structure (1):

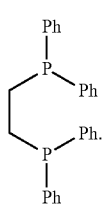

(1)

In one variant of the process, the ligand is added in a molar ratio to cobalt of L/Co=<0.90/1.
In one variant of the process, the ligand is added in a molar ratio to cobalt of L/Co=<0.80/1.
In one variant of the process, the ligand is added in a molar ratio to cobalt of L/Co=<0.70/1.
In one variant of the process, the ligand is added in a molar ratio to cobalt of L/Co=<0.60/1.
In one variant of the process, the ligand is added in a molar ratio to cobalt of L/Co=<0.50/1.
In one variant of the process, the ligand is added in a molar ratio to cobalt of L/Co=<0.40/1.
In one variant of the process, the ligand is added in a molar ratio to cobalt of L/Co=<0.30/1.
In one variant of the process, the ligand is added in a molar ratio to cobalt of L/Co=<0.20/1.

In one variant of the process, the cobalt precatalyst is initially charged in the form of a solution.

In one variant of the process, the olefin is added to the initially charged cobalt precatalyst solution.

In one variant of the process, the syngas in process step d) is supplied at a pressure within a range from 1 to 8 MPa (10 to 80 bar).

In one variant of the process, the syngas in process step d) is supplied at a pressure within a range from 4 to 6 MPa (40 to 60 bar).

In one variant of the process, the heating of the reaction mixture in process step e) is to a temperature within a range from 80° C. to 180° C.

In one variant of the process, the heating of the reaction mixture in process step e) is to a temperature within a range from 120° C. to 160° C.

In one variant of the process, the cobalt precatalyst is $[Co(acac)(C_4H_8O_2)_4]^+[BF_4]^-$ (V1).

In one variant of the process, the olefin is selected from: ethene, propene, 1-butene, cis-2-butene, trans-2-butene, mixture of cis- and trans-2-butene, raffinate 1, raffinate 2, isobutene, 1-pentene, 2-pentene, 2-methyl-1-butene, 2-methyl-2-butene, 1-methylcyclohexene, tetramethylethene, 1-octene, 2-octenes, cyclooctene, di-n-butene, diisobutene, undecenes, dodecenes, triisobutene, tri-n-butene.

In one variant of the process, the olefin is selected from: 1-butene, cis-2-butene, trans-2-butene, isobutene, 1-pentene, 2-pentene, 1-octene, 2-octenes, di-n-butene, diisobutene, triisobutene, tri-n-butene.

The invention shall be elucidated in more detail hereinbelow with reference to a working example.

Hydroformylation of 1-octene with [Co(acac)($C_4H_8O_2$)](BF$_4$)

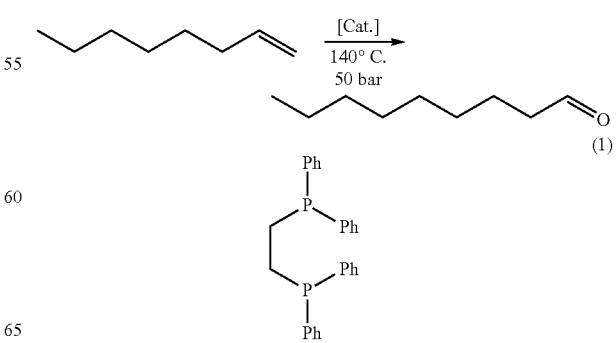

(1)

(1): 1,2-Bis(diphenylphosphino)ethane (DPPE)

(V1): [Co(acac)($C_4H_8O_2$)]($BF_4$)

A solution of the Co precatalyst (V1) and diphosphine (1) in diglyme (24 mL) was introduced into a 150 mL Premex autoclave with sparging stirrer and pressurized with 32 bar of syngas. The solution was heated to 160° C. and the pressure readjusted to 50 bar. After 5 minutes, the temperature was lowered to 140° C. The olefin (4.74 mL) was then added to the catalyst solution by means of a pressure pipette and the reaction solution (1 M olefin) stirred at 50 bar and 140° C. The reaction mixture was then cooled to room temperature and the pressure released. The yields were determined by gas chromatography.

Reaction Conditions:

[Co]: 2.6 mM, T: 140° C., p(syngas): 50 bar, t: 1 h, precatalyst: V1

Hydroformylation of 1-octene

| Ligand | Precatalyst | P/Co | L/Co | T (° C.) | t (h) | Yield (%) |
|---|---|---|---|---|---|---|
| (1) | V1 | 2:1 | 1:1 | 140 | 1 | 35.9 |
| (1)* | V1 | 0.23:1 | 0.115:1 | 140 | 1 | 69.9 |

*process according to the invention

With the ligand-cobalt ratio (L/Co) according to the invention, it was possible to increase the yield.

As demonstrated by the working example, the object is achieved by the process according to the invention.

The invention claimed is:

1. A process comprising the process steps of:
    a) adding an olefin;
    b) adding a cobalt precatalyst;
    c) adding a ligand (L) having the structure (I):

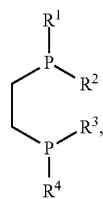

(I)

where $R^1$, $R^2$, $R^3$ and $R^4$ are selected from:
—H, —($C_1$-$C_{12}$)-alkyl or —($C_6$-$C_{20}$)-aryl;
wherein the ligand is added in a molar ratio to cobalt of L/Co=<0.95/1;
    d) supplying of syngas;
    e) heating the reaction mixture from a) to d), to convert the olefin into an aldehyde.

2. The process according to claim 1, where $R^1$, $R^2$, $R^3$ and $R^4$ are selected from: —($C_1$-$C_{12}$)-alkyl or —($C_6$-$C_{20}$)-aryl.

3. The process according to claim 1, where $R^1$ and $R^2$ are -Ph.

4. The process according to claim 1, where $R^1$ and $R^3$ are -Ph.

5. The process according to claim 1, where the ligand has the structure (1):

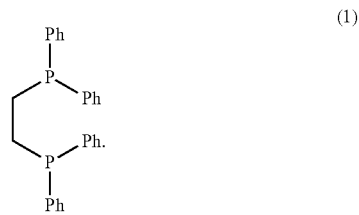 [SMILES: c1ccc(P(CCP(c2ccccc2)c2ccccc2)c2ccccc2)cc1]

(1)

6. The process according to claim 1, wherein the ligand is added in a molar ratio to cobalt of L/Co=<0.90/1.

7. The process according to claim 1, wherein the ligand is added in a molar ratio to cobalt of L/Co=<0.80/1.

8. The process according to claim 1, wherein the Co precatalyst is initially charged in the form of a solution.

9. The process according to claim 8, wherein the olefin is added to the initially charged Co precatalyst solution.

10. The process according to claim 1, wherein the syngas is supplied in process step d) at a pressure within a range from 1 to 8 MPa (10 to 80 bar).

11. The process according to claim 1, wherein the heating of the reaction mixture in process step e) is to a temperature within a range from 80° C. to 180° C.

12. The process according to claim 1, wherein the cobalt precatalyst is [Co(acac)($C_4H_8O_2$)$_4$]$^+$ [$BF_4$]$^-$ (V1).

13. The process according to claim 1, wherein the olefin is selected from:
ethene, propene, 1-butene, cis-2-butene, trans-2-butene, mixture of cis- and trans-2-butene, raffinate 1, raffinate 2, isobutene, 1-pentene, 2-pentene, 2-methyl-1-butene, 2-methyl-2-butene, 1-methylcyclohexene, tetramethylethene, 1-octene, 2-octenes, cyclooctene, di-n-butene, diisobutene, undecenes, dodecenes, triisobutene or tri-n-butene.

* * * * *